(12) United States Patent
Vogler et al.

(10) Patent No.: US 8,425,498 B2
(45) Date of Patent: Apr. 23, 2013

(54) APPARATUS FOR TREATMENT OF MATERIAL, IN PARTICULAR FOR REFRACTIVE SURGERY

(75) Inventors: Klaus Vogler, Eckental (DE); Christof Donitzky, Eckental (DE)

(73) Assignee: Wavelight AG, Erlangen (DE)

( * ) Notice: Subject to any disclaimer, the term of this patent is extended or adjusted under 35 U.S.C. 154(b) by 1420 days.

(21) Appl. No.: 12/061,862

(22) Filed: Apr. 3, 2008

(65) Prior Publication Data

US 2008/0249513 A1 Oct. 9, 2008

(30) Foreign Application Priority Data

Apr. 4, 2007 (EP) .................................. 07007119

(51) Int. Cl.
*A61B 18/18* (2006.01)

(52) U.S. Cl.
USPC ............................................................ 606/5

(58) Field of Classification Search ................ 606/1–19
See application file for complete search history.

(56) References Cited

U.S. PATENT DOCUMENTS

| 2001/0037105 | A1* | 11/2001 | Lin ................................... 606/5 |
| 2005/0085800 | A1 | 4/2005 | Lenzner et al. |
| 2005/0245915 | A1 | 11/2005 | Loesel et al. |
| 2006/0095023 | A1 | 5/2006 | Loesel et al. |
| 2007/0010804 | A1* | 1/2007 | Rathjen et al. ................... 606/5 |
| 2007/0055221 | A1* | 3/2007 | Lubatschowski et al. ........ 606/5 |

FOREIGN PATENT DOCUMENTS

| CN | 1891184 | 1/2007 |
| EP | 1731120 | 12/2006 |
| RU | 2282425 C1 | 8/2006 |
| WO | 03011175 A2 | 2/2003 |

OTHER PUBLICATIONS

Chinese Patent Office, Office Action dated Aug. 24, 2011, Application No. 200880011234.9, 7 pages.
Patent Cooperation Treaty—European Patent Office, "Notification of Transmittal of the International Search Report and the Written Opinion of the International Searching Authority, or the Declaration," International Application No. PCT/EP2008/002658, Jun. 19, 2008, 11 pages.
The Federal Service for Intellectual Property, Patents and Trademarks, "Decision on Granting a Patent for Invention," Aug. 13, 2012, 4 pages, Moscow, RU.

* cited by examiner

*Primary Examiner* — Bethany Barham
(74) *Attorney, Agent, or Firm* — Haynes and Boone, LLP

(57) ABSTRACT

A device and a computer program for material processing, in particular refractive eye surgery, operate with a pulsed femtosecond laser and the individual focal points are positioned in such a way that the spacings of neighboring focal points for the most part vary, in order to avoid a regular grating structure avoiding undesired diffraction phenomena.

20 Claims, 1 Drawing Sheet

APPARATUS FOR TREATMENT OF MATERIAL, IN PARTICULAR FOR REFRACTIVE SURGERY

Figure 2:
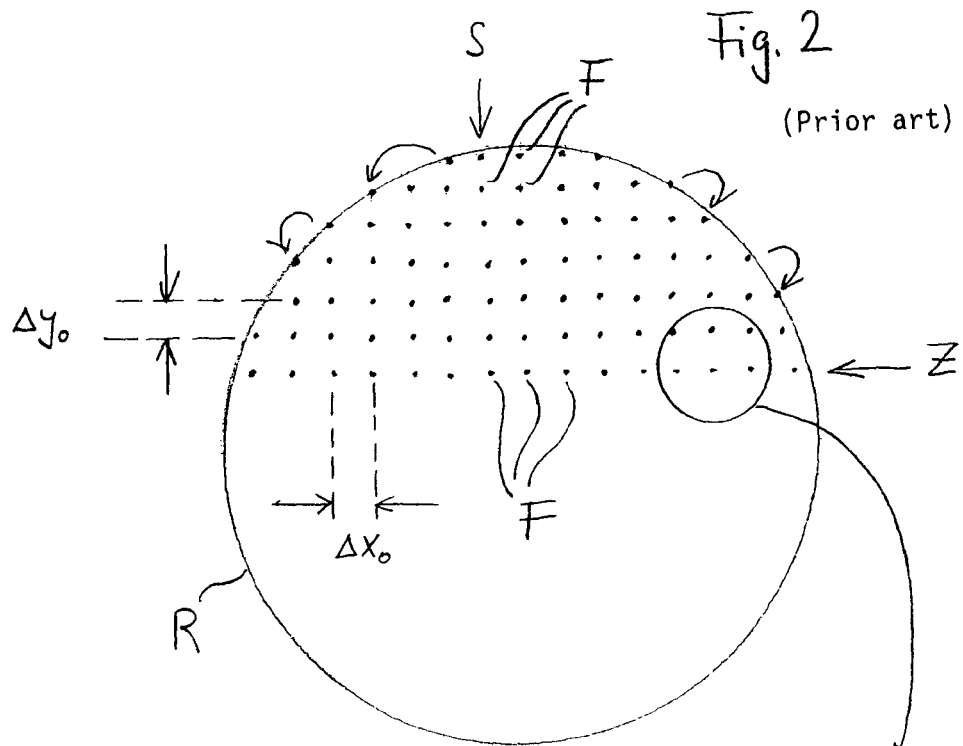

This application claims priority of European Patent Application Number 07007119.6, filed Apr. 4, 2007, entitled "Apparatus for Treatment of Material, in Particular for Refractive Surgery," the entirety of which is incorporated herein by this reference.

The invention relates to a device for material processing, in particular refractive eye surgery, having a pulsed laser beam source, means for focusing and guiding the laser beam emitted by the laser beam source onto material to be processed, in particular an eye, and having a computer-assisted controller for controlling the guide means so that the focal points of the laser beam are guided on a controlled path.

The invention will be described below with a view to refractive eye surgery, in particular with a view to LASIK.

LASIK is a method of refractive surgery which has now become widely established. During refractive surgery, the refractive properties of the eye are modified by laser radiation.

An instrument which is increasingly gaining importance in LASIK is the femtosecond laser, i.e. a pulsed laser with extremely short pulse lengths which may lie in the range of up to a few hundred femtoseconds. Owing to these short pulse lengths, by focusing the radiation within very small volumes it is possible to produce extremely high power densities of the electromagnetic radiation and therefore extremely high field strengths. The femtosecond laser is currently used in LASIK primarily as an instrument to produce the so-called flap cut, i.e. a cut through the cornea to produce a flap which generally remains connected to the cornea by a small edge piece so that it can be folded away in order to expose underlying stroma, which is then removed by a (different) laser beam according to a previously calculated ablation profile. After this reshaping of the cornea, the flap is folded back into place and generally heals very rapidly again with the cornea. The femtosecond laser is increasingly replacing the microkeratome. The microkeratome is a mechanical device with an oscillating blade, by which it is likewise possible to make the aforementioned cut in order to produce the flap.

It is estimated that more than 1 million operations of this type have to date been carried out worldwide with a femtosecond laser.

Use of the femtosecond laser for the aforementioned cutting in the cornea is also referred to as fs-LASIK. Compared with the use of a mechanical microkeratome, fs-LASIK has a range of advantages, for example a lower complication risk, a higher accuracy of the desired cutting thickness of the flap and also a better shaped edge section.

Yet in order to achieve a quality of the cutting bed with an fs laser as with the precise blade of a microkeratome and also to permit separation of the flap without complications after the cutting, in fs-LASIK the parameters of the method must be optimised very finely, in particular the cutting parameters (see below).

The reason for this requisite fine optimisation of fs-LASIK resides in the physics of generating the cut. Basically, the fs-LASIK cut is made by a tightly arranged sequence of small so-called microdissections, for example with a diameter in the range of 5 μm. The tissue is disrupted by the extremely high local power density of the radiation (i.e. the high field strength), and local penetration of the corneal tissue and the microfibrils contained therein takes place. Together, the set of closely neighbouring focused pulses finally lead to extensive penetration of the tissue. With currently available lasers, the requisite field strengths are generally achieved only at the focus. This in turn has the advantage that the tissue penetration may also be induced at a depth below the tissue surface, precisely at the position of the focal point.

The aforementioned method parameters to be optimised very sensitively are in particular the laser pulse energy, the focal point diameter, the focal point spacing, and the control of the individual focused pulses in time and space.

For carrying out fs-LASIK cutting with a sequence of tightly neighbouring microdissections by close placement and chronological succession of focal points guided on a path, there are various approaches in the prior art. The time taken to perform the entire cutting to produce the flap is also a criterion.

The prior art comprises, for example, guidance of the focal points of the individual radiation puzzle from pulse to pulse along a spirally shaped path, and in particular also linewise guidance of the chronologically successive focal points, similarly for instance to the control of an electron beam in a conventional cathode ray tube.

The means by which the laser radiation is shaped and guided in space for the purposes described above are known in the prior art. The aforementioned linewise rastering of the focal points is widely used because available scanning techniques (mirrors and their controls) can be employed for this. In order to produce a good fs-LASIK cut with such linewise guidance of the focal points of successive laser radiation pulses, the following method parameters may for example be suitable:

| | |
|---|---|
| laser pulse energy: | 1 μJ |
| focus diameter: | <5 μm |
| focus spacing in the row: | ~8 μm |
| row spacing: | ~12 μm |
| diameter of the flap: | 9 mm |
| laser pulse repetition frequency: | 60 kHz |

With these parameters, for example, a flap cut can be achieved in less than 30 seconds.

In connection with fs-LASIK cuts, however, a phenomenon has recently arisen which irritates patients treated in this way. After an fs-LASIK operation, patients occasionally see chromatically resolved edge structures at sharp edges of objects, i.e. a kind of rainbow. This is referred to as the rainbow effect.

It is an object of the invention to avoid such a rainbow effect.

For use in refractive eye surgery, the invention achieves this by a device having a pulsed laser beam source, means for focusing and guiding the laser beam emitted by the laser beam source onto an eye, and a computer-assisted controller for controlling the guide means so that the focal points of the guided laser beam are guided on a predetermined path on or in the eye, wherein the spacings of neighbouring focal points vary at least for the most part.

The invention is not restricted to use in refractive surgery, rather it may generally be used in material processing wherever the said rainbow effects may occur, for example in the processing of optical components or the like.

To this end, the invention generally teaches a computer program for controlling a material-processing device, the device having: a pulsed laser beam source, means for guiding and focusing the laser beam emitted by the laser beam source onto material to be processed, a computer-assisted controller for controlling the guide means so that the focal points of the laser beam are guided on a predetermined path on or in the material, wherein the spacings of neighbouring focal points on or in the material vary at least for the most part.

The invention is based on the assumption that the said rainbow effects occur because, with conventional control of the spatial positions of the radiation focal points, structures are produced in the processed material i.e. particularly in the cornea, which thereupon act physically for example like a grating that decomposes white light passing through into its spectral components by diffraction. In other words: in the prior art, the spatial positioning selected therein for the individual radiation focal points creates regular structures with equidistant focal point spacings that may in particular form a two-dimensional grating, which produces diffraction images for example on the retina in the eye so that the individual colours of the white light no longer lie precisely on one another when a sharp edge is being observed.

It will be understood that this effect is extremely undesirable in refractive surgery.

According to the invention, the spacings of neighbouring focal points are selected so that the said regular structures no longer occur in the processed material, particularly in a cornea. In other words: according to the invention the individual points of action of the laser radiation are positioned so that no regular structures, which cause undesired diffraction phenomena, occur any longer.

In the case of the conventional type of fs-LASIK, such regular structures causing the undesired diffraction effect were created because of the individual focal points of the laser radiation essentially being positioned equidistantly, so that regular grating structures with local variation of the refractive index remained even after the flap was folded back into place and the healing process was completed.

According to a preferred configuration of the invention, the spacings of neighbouring focal points are varied stochastically. To calculate the individual positions of spatially successive focal points, for example, a basic spacing that remains constant in the calculation may be specified, which is then varied from pulse to pulse within predetermined small limits. The predetermined deviation limits (i.e. the limits of the deviation from an equidistant focal point sequence) are selected so that the focal points thereupon produce a clean cut despite their nonuniform spacings. For example, the deviation limits may be set at from 5 to 20% of the constant of the computational basic grating, the grating constant of the computational basic grating being small enough to entail uninterrupted microdissections even with the greatest possible spacing of the focal point positions thus generated.

Figure 3:
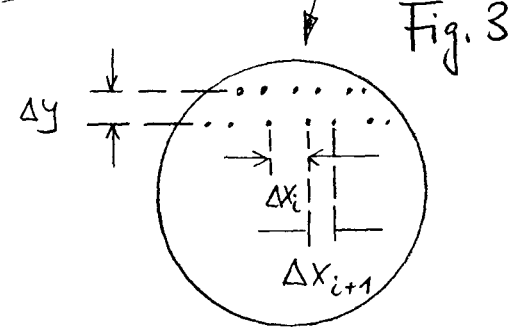
Figure 1:
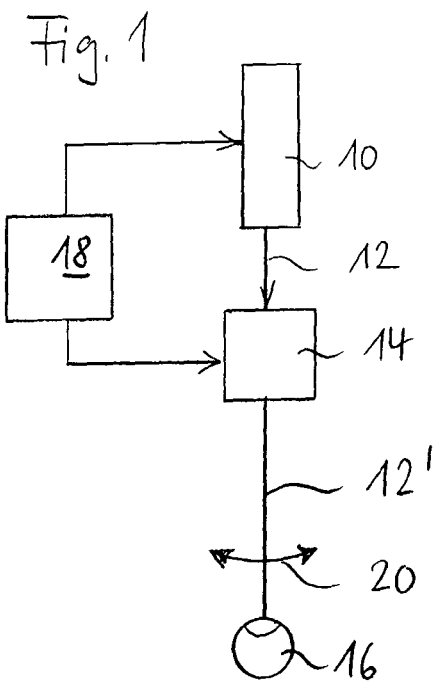

An exemplary embodiment of the invention will be described in more detail below with the aid of the drawing, in which:

FIG. 1 schematically shows a device for refractive eye surgery;

FIG. 2 shows an exemplary embodiment of a path, according to which focal points of fs laser pulses in a cornea are controlled in chronological succession in a cornea; and FIG. 3 shows a detail of FIG. 2, the regular equidistance between individual focal point positions being broken.

FIG. 1 schematically shows a device known per se for refractive eye surgery, having a laser beam source 10 for generating laser pulses with pulse lengths in the femtosecond range, the emitted pulses being indicated by the reference 12. The laser pulses are directed in means 14 for shaping, in particular focusing, and guiding the laser beam pulses 12' in the direction of an eye 16. The means for shaping, focusing and guiding the radiation are likewise known per se. A computer-assisted controller 18 controls the laser beam source and the means 14 for beam shaping and guiding. For example, the laser beam pulses 12' are guided according to the arrow 20 over the eye to be refractively treated. Since the radiation pulses are discrete pulses, this guiding over the eye may also be referred to as "rastering".

FIG. 2 schematically shows such rastering of the focal points F for an fs-LASIK cut. The edge of the cut is denoted by R. For example, the cut may have a diameter of 9 mm. The individual focal points F are represented only in the upper half in FIG. 2, although the lower half of the focal points is to be regarded as continuing in the same way.

The focal points F of the chronologically sequential laser pulses 12' are guided in rows Z, the jumps between rows being marked by arrows. The chronological order of the pulses thus runs linearly in rows from right to left or left to right. As shown in FIG. 2, this leads to a regular grating structure in which neighbouring focal points F in a row Z always have the same spacing $\Delta x_0$. The spacing $\Delta y_0$ between the rows is also constant. As mentioned above, it is this regular grating structure which is to be avoided.

To this end, in the exemplary embodiment represented according to FIG. 3, the spacings $\Delta x$ between neighbouring focal point positions are varied in a row Z. For example, the represented spacing $\Delta x_i$ of two neighbouring focal points F is greater than the spacing $\Delta x_{i+1}$ in the subsequent interval between two focal points.

This variation of spacings is carried out irregularly over each of the rows for at least a majority of the focal point spacings. The stipulation "at least for a majority" is to be selected so that overall no sufficiently regular grating structure is formed, which can generate perturbing diffraction effects in the sense described above. According to this guideline, a few equidistant focal point positions do not cause problems.

One possible way of varying the focus spacing $\Delta x$ within a row is the following stochastic approach:

| | |
|---|---|
| $\Delta x_i = \Delta x_0 + a(i \cdot \Delta x_0)$ | between the $(i-1)^{th}$ focus and the $i^{th}$ focus |
| $\Delta x_{i+1} = \Delta x_0 + a[(i+1) \cdot \Delta x_0]$ | between the $i^{th}$ and $(i+1)^{th}$ foci |
| e.g. $\Delta x_0$ = const = 5 μm | |
| a = 0.10 | percentage modulation rate |
| I; (I + 1) | generated random numbers between 0 ... 1 |

$\Delta x_0$ is the purely computationally specified basic spacing of neighbouring foci (focal points) in a row Z. This spacing is varied stochastically, i.e. according to a random sequence, within limits according to the formula above. For example, the computational basic spacing $\Delta x_0$ is 5 μm with a focus diameter of 3 μm. The factor a specifies the limits for the permissible variation in the spacing of neighbouring foci. If a is 0.10, then the permissible variation of the focus spacings is 10%. The factor a thus determines the modulation limits of the focus spacings. The values i, (i+1) are random numbers generated by a random generator in the number interval [0 . . . 1], which stochastically determine the spacing of neighbouring foci for the individual case. The parameters $\Delta x_0$, a, i are selected so that despite the spacing variations, the focal points lie sufficiently close to one another in order to produce a highly coherent, "continuous" cutting bed.

What is crucial is that the variation in the focus spacings now ensures that a diffraction image, which is perturbing to the application in question, can no longer be created by a regular grating structure.

Similarly, either on is own or in addition to the variation of the spacings in a row, the focal point spacing in the columns S could also be varied. Correspondingly, the regularity of the focus spacings in the y direction could thus be broken as follows:

| | |
|---|---|
| $\Delta y_i = \Delta y_0 + b(i \cdot \Delta y_0)$ | line spacing between the $(i-1)^{th}$ row and the $i^{th}$ row |
| $\Delta y_{i+1} = \Delta y_0 + b[(i+1) \cdot \Delta y_0]$ | line spacing between $i^{th}$ and $(i+1)^{th}$ rows |
| e.g. $b = 0.15$ | modulation width |
| $\Delta y_0 = 10\ \mu m$ | row spacing |

The individual parameters have similar meanings as described above with reference to the spacing variations in the row Z. The factor b of 0.15 thus specifies the limits for the spacing variation in the y direction, i.e. 15% here, and $\Delta y_0$ is the computationally specified basic spacing of focal points in the column S. Here again, the individual parameters must be selected and optimised so that a very highly coherent cutting surface is obtained in all cases with the predetermined focus diameter and the pulse energy set for the fs laser.

Overall, this results in a residual roughness remaining in the cutting bed with density variations, which however are sufficiently irregular to prevent undesired diffraction effects.

Theoretically the above-described effect of focal point spacings that vary, which are obtained computationally by means of a random generator or the like, may conceivably also be obtained at least partially by mechanically unstable beam guiding, although computational control and management of the process is to be preferred.

The invention claimed is:

1. A device for refractive eye surgery, comprising:
a pulsed laser beam source,
focusing optics to focus and guide the laser beam emitted by the pulsed laser beam source onto an eye, and
a computer-assisted controller for controlling the focusing optics so that the foci of the guided laser beam are guided on a predetermined path on or in the eye, wherein the predetermined path includes a plurality of lines, each of the plurality of lines extending parallel to a common axis,
wherein spacings of neighboring lines of the plurality of parallel lines of the predetermined path are varied such that the plurality of lines extending parallel to the common axis are spaced equally in a direction perpendicular to the common axis and the spacings of the neighboring foci in each line vary stochastically but within a predetermined deviation limit relative to a focal point spacing constant.

2. A device for refractive eye surgery, comprising:
a pulsed laser beam source,
focusing optics to focus and guide the laser beam emitted by the laser beam source onto an eye,
a computer-assisted controller for controlling the guide means so that the foci of the guided laser beam are guided on a predetermined path on or in the eye, wherein the predetermined path includes a plurality of lines, each of the plurality of lines extending parallel to a common axis,
wherein spacings between neighbouring lines of the plurality of parallel lines of the predetermined path vary such that the plurality of lines extending parallel to the common axis are spaced irregularly in a direction perpendicular to the common axis and wherein the spacings of the neighboring foci in each line vary stochastically along the axis of each line within a predetermined deviation limit relative to a focal point spacing constant.

3. The device of claim 1, wherein the pulsed laser beam source is a femtosecond laser.

4. The device of claim 1, wherein the predetermined path of the foci is calculated for a LASIK flap cut.

5. The device of claim 1, wherein the predetermined deviation limit is between 5% and 20% of the focal point spacing constant.

6. The device of claim 1, wherein the predetermined deviation limit is 10%.

7. The device of claim 1, wherein the spacing between a first focus and a second focus of a line of the plurality of lines is determined by adding a first variable to the focal point spacing constant.

8. The device of claim 7, wherein the spacing between the second focus and a third focus of the line of the plurality of lines is determined by adding a second variable to the focal point spacing constant.

9. The device of claim 8, wherein the first variable and the second variable are calculated using a random number generator.

10. The device of claim 8, wherein the first variable and the second variable are calculated using a constant that limits the spacing between the first focus and the second focus and the spacing between the second focus and the third focus to be within the predetermined deviation limit.

11. The device of claim 10, wherein the predetermined deviation limit is between 5% and 20% of the focal point spacing constant.

12. The device of claim 2, wherein the pulsed laser beam source is a femtosecond laser.

13. The device of claim 2, wherein the predetermined path is calculated for a LASIK procedure.

14. The device of claim 2, wherein the predetermined deviation limit is between 5% and 20% of the focal point spacing constant.

15. The device of claim 2, wherein the spacing between a first focus and a second focus of a line of the plurality of lines is determined by adding a first variable to the focal point spacing constant and wherein the spacing between the second focus and a third focus of the line of the plurality of lines is determined by adding a second variable to the focal point spacing constant.

16. The device of claim 15, wherein the first variable and the second variable are calculated using a random number generator.

17. The device of claim 15, wherein the first variable and the second variable are calculated using a constant that limits the spacing between the first focus and the second focus and the spacing between the second focus and the third focus to be within the predetermined deviation limit.

18. A system for performing eye surgery, the system comprising:
a laser source and associated focusing optics for emitting a laser beam towards an eye to be treated; and
a control system configured to control a focal point of the laser beam along a surgical path in accordance with executable instructions stored in a non-transitory computer readable medium, the executable instructions including:
instructions for defining a predetermined path for the laser beam,
wherein the predetermined path including a plurality of lines extending parallel to a common axis, and
wherein spacings between adjacent foci along each line of the plurality of lines are varied within a predetermined deviation limit relative to a focal point spacing constant so that the foci are positioned such that regular structures that would cause an undesired defraction phenomena do not occur.

19. The system of claim 18, wherein spacings between adjacent lines of the predetermined path are spaced equally in a direction perpendicular to the common axis.

20. The system of claim 18, wherein spacings between adjacent lines of the predetermined path are varied in a direction perpendicular to the common axis.

* * * * *